(12) United States Patent
Oomura et al.

(10) Patent No.: US 6,518,235 B1
(45) Date of Patent: Feb. 11, 2003

(54) METHODS FOR IMPROVING BRAIN FUNCTION USING LEPTIN OR ANALOGS THEREOF

(76) Inventors: Yutaka Oomura, 6-14-17, Kawamo, Takarazuka-shi, Hyogo-ken (JP); Nobuaki Hori, 1-3-6-305, Chidori, Koga-shi, Fukuoka-ken (JP); Takemasa Shiraishi, 8-19-2, Kamitsuruma, Sagamihara-shi, Kanagawa-ken (JP); Kazuo Sasaki, 5-1-14, Sengoku-cho, Toyama-shi, Toyaam-ken (JP); Hiroshi Takeda, 5-2, Higashiyama-cho, Itabashi-ku, Tokyo-to (JP); Minoru Tsuji, 3-23-12-104, Kamiikedai, Ota-ku, Tokyo-to (JP); Teruhiko Matsumiya, 3-41-25, Ogikubo, Suginami-ku, Tokyo-to (JP)

( * ) Notice: Subject to any disclaimer, the term of this patent is extended or adjusted under 35 U.S.C. 154(b) by 0 days.

(21) Appl. No.: 09/200,919

(22) Filed: Nov. 30, 1998

(30) Foreign Application Priority Data

Mar. 26, 1998 (JP) .......................... 10-100202

(51) Int. Cl.⁷ .................. A01N 37/18; A61K 38/00; C07K 1/00; C07K 14/00; C07K 17/00
(52) U.S. Cl. .............. 514/2; 530/350; 514/12
(58) Field of Search .................. 514/2, 12; 530/350

(56) References Cited

U.S. PATENT DOCUMENTS 5,756,461 A * 5/1998 Stephens et al.
5,830,450 A * 11/1998 Lallone

OTHER PUBLICATIONS

Rudingder J. In. Peptide Hormones. ed. JA Parsons. Baltimore, University Park Press, 1976, pp. 1–7.*
Hefti, F. and Knusel, B. Neurobiology of Aging. 9:689–690, 1988.*
Sansone et al., "Effects of Oxiracetam, Physostigmine, and Their Combination on Active and Passive Avoidance Learning in Mice," *Pharmacology Biochemistry and Behavior* vol. 44, pp. 451–455, 1993.
Nakagawa et al., "Muscimol induces state–dependent learning in Morris water maze task in rats," *Brain Research*, 681 (1995) 126–130.
Ito et al., "Effects of physostigmine and scopolamine on long–term potentiation of hippocampal population spikes in rats," *Can. J. Physiol. Pharmacol.*, 66: 1010–1016 (1988).
Riedel et al., "Metabotropic glutamate receptors in hippocampal long–term potentiation and learning and memory," *Acta Physiol. Scand.*, 157(1):1–19 (May 1996), abstract.
Davis et al., "Enhancement of memory processes in Alzheimer's disease with multiple–dose intravenous physostigmine," *Am J. Psychiatry*, 139(11): 1421–4 (Nov. 1982), abstract.
Stern et al., "Long–term administration of oral physostigmine in Alzheimer's disease," *Neurology*, 38(12):1837–41 (Dec. 1988), abstract.
Levy et al., "Transdermal physostigmine in the treatment of Alzheimer's disease," *Alzheimer Dis. Assoc. Disord.*, 8(1): 15–21 (Spring 1994), abstract.
Sahakian et al., "Cholinergic effects on constructional abilities and on mnemonic processes; a case report," *Psychol. Med.*, 17(2):329–33 (May 1987), abstract.
Kark et al., "Physostigmine in familial ataxias," *Neurology*, 27(1):70–2 (Jan. 1977), abstract.
Aschoff, et al., "Physostigmine in treatment of cerebellar ataxia," *Nervenarzt*, 67(4):311–8 (Apr. 1996), abstract.
Davis et al., "Pharmacological Investigations of the cholinergic Imbalance hypotheses of movement disorders and psychosis," *Biol. Psychiatry*, 13(1):23–49 (Feb. 1978), abstract.
Nilsson et al., "Hemodynamic responses to physostigmine in patients with a drug overdose," *Anesth. Analg.*, 62(10):885–8 (Oct. 1983), abstract.
Aquilonius et al., "the use of physostigmine as an antidote in tricyclic anti–depressant intoxication," *Acta Anaesthesiol. Scand.*, 22(1):40–5 (1978), abstract.
Schneck et al., "Central anticholinergic syndrome (CAS) in anesthesia and intensive care," *Acta Anaesthesiol Belg.*, 40(3):219–28 (1989), abstract.

* cited by examiner

Primary Examiner—Gary Kunz
Assistant Examiner—Robert S. Landsman
(74) Attorney, Agent, or Firm—Hollander Law Firm, P.L.C.

(57) ABSTRACT

The present invention is to provide a drug for improvement of brain function which is effective to prevent from or to cure dementia such as Alzheimer's disease. The drug for improvement of brain function of this invention comprises leptin of mammals as an effective component wherefore has a superior effect in improvement of learning and memory.

12 Claims, 7 Drawing Sheets

SEQUENCE LISTING

<160> NUMBER OF SEQ ID NOS: 6

<210> SEQ ID NO 1
<211> LENGTH: 146
<212> TYPE: PRT
<213> ORGANISM: HUMAN

<400> SEQUENCE: 1

```
Val Pro Ile Gln Lys Val Gln Asp Asp Thr Lys Thr Leu Ile Lys Thr
 1               5                  10                  15

Ile Val Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Gln Ile Ser Asn Asp Leu
    65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145
```

<210> SEQ ID NO 2
<211> LENGTH: 146
<212> TYPE: PRT
<213> ORGANISM: MOUSE

<400> SEQUENCE: 2

```
Val Pro Ile Gln Lys Val Gln Asp Asp Thr Lys Thr Leu Ile Lys Thr
 1               5                  10                  15

Ile Val Thr Arg Ile Asn Asp Ile Ser His Thr Gln Ser Val Ser Ala
                20                  25                  30

Lys Gln Arg Val Thr Gly Leu Asp Phe Ile Pro Gly Leu His Pro Ile
            35                  40                  45

Leu Ser Leu Ser Lys Met Asp Gln Thr Leu Ala Val Tyr Gln Gln Val
        50                  55                  60

Leu Thr Ser Leu Pro Ser Gln Asn Val Leu Gln Ile Ala Asn Asp Leu
    65                  70                  75                  80

Glu Asn Leu Arg Asp Leu Leu His Leu Leu Ala Phe Ser Lys Ser Cys
                85                  90                  95

Ser Leu Pro Gln Thr Ser Gly Leu Gln Lys Pro Glu Ser Leu Asp Gly
            100                 105                 110

Val Leu Glu Ala Ser Leu Tyr Ser Thr Glu Val Val Ala Leu Ser Arg
        115                 120                 125

Leu Gln Gly Ser Leu Gln Asp Ile Leu Gln Gln Leu Asp Val Ser Pro
    130                 135                 140

Glu Cys
145
```

<210> SEQ ID NO 3
<211> LENGTH: 146
<212> TYPE: PRT
<213> ORGANISM: RAT

<400> SEQUENCE: 3

Val Pro Ile His Lys Val Gln Asp Asp Thr Lys Thr Leu Ile Lys Thr
 1               5                  10                  15
Ile Val Thr Arg Ile Asn Asp Ile Ser His Thr Gln Ser Val Ser Ala
                20                  25                  30
Arg Gln Arg Val Thr Gly Leu Asp Phe Ile Pro Gly Leu His Pro Ile
            35                  40                  45
Leu Ser Leu Ser Lys Met Asp Gln Thr Leu Ala Val Tyr Gln Gln Ile
    50                  55                  60
Leu Thr Ser Leu Pro Ser Gln Asn Val Leu Gln Ile Ala His Asp Leu
65                  70                  75                  80
Glu Asn Leu Arg Asp Leu Leu His Leu Leu Ala Phe Ser Lys Ser Cys
                85                  90                  95
Ser Leu Pro Gln Thr Arg Gly Leu Gln Lys Pro Glu Ser Leu Asp Gly
            100                 105                 110
Val Leu Glu Ala Ser Leu Tyr Ser Thr Glu Val Val Ala Leu Ser Arg
        115                 120                 125
Leu Gln Gly Ser Leu Gln Asp Ile Leu Gln Gln Leu Asp Leu Ser Pro
    130                 135                 140
Glu Cys
145

<210> SEQ ID NO 4
<211> LENGTH: 147
<212> TYPE: PRT
<213> ORGANISM: HUMAN

<400> SEQUENCE: 4

Met Val Pro Ile Gln Lys Val Gln Asp Asp Thr Lys Thr Leu Ile Lys
 1               5                  10                  15
Thr Ile Val Thr Arg Ile Asn Asp Ile Ser His Thr Gln Ser Val Ser
                20                  25                  30
Ser Lys Gln Lys Val Thr Gly Leu Asp Phe Ile Pro Gly Leu His Pro
            35                  40                  45
Ile Leu Thr Leu Ser Lys Met Asp Gln Thr Leu Ala Val Tyr Gln Gln
    50                  55                  60
Ile Leu Thr Ser Met Pro Ser Arg Asn Val Ile Gln Ile Ser Asn Asp
65                  70                  75                  80
Leu Glu Asn Leu Arg Asp Leu Leu His Val Leu Ala Phe Ser Lys Ser
                85                  90                  95
Cys His Leu Pro Trp Ala Ser Gly Leu Glu Thr Leu Asp Ser Leu Gly
            100                 105                 110
Gly Val Leu Glu Ala Ser Gly Tyr Ser Thr Glu Val Val Ala Leu Ser
        115                 120                 125
Arg Leu Gln Gly Ser Leu Gln Asp Met Leu Trp Gln Leu Asp Leu Ser
    130                 135                 140
Pro Gly Cys
145

<210> SEQ ID NO 5

```
<211> LENGTH: 147
<212> TYPE: PRT
<213> ORGANISM: MOUSE

<400> SEQUENCE: 5

Met Val Pro Ile Gln Lys Val Gln Asp Asp Thr Lys Thr Leu Ile Lys
 1               5                  10                  15

Thr Ile Val Thr Arg Ile Asn Asp Ile Ser His Thr Gln Ser Val Ser
             20                  25                  30

Ala Lys Gln Arg Val Thr Gly Leu Asp Phe Ile Pro Gly Leu His Pro
         35                  40                  45

Ile Leu Ser Leu Ser Lys Met Asp Gln Thr Leu Ala Val Tyr Gln Gln
     50                  55                  60

Val Leu Thr Ser Leu Pro Ser Gln Asn Val Leu Gln Ile Ala Asn Asp
 65                  70                  75                  80

Leu Glu Asn Leu Arg Asp Leu Leu His Leu Leu Ala Phe Ser Lys Ser
                 85                  90                  95

Cys Ser Leu Pro Gln Thr Ser Gly Leu Gln Lys Pro Glu Ser Leu Asp
                100                 105                 110

Gly Val Leu Glu Ala Ser Leu Tyr Ser Thr Glu Val Val Ala Leu Ser
            115                 120                 125

Arg Leu Gln Gly Ser Leu Gln Asp Ile Leu Gln Gln Leu Asp Val Ser
        130                 135                 140

Pro Glu Cys
145

<210> SEQ ID NO 6
<211> LENGTH: 147
<212> TYPE: PRT
<213> ORGANISM: RAT

<400> SEQUENCE: 6

Met Val Pro Ile His Lys Val Gln Asp Asp Thr Lys Thr Leu Ile Lys
 1               5                  10                  15

Thr Ile Val Thr Arg Ile Asn Asp Ile Ser His Thr Gln Ser Val Ser
             20                  25                  30

Ala Arg Gln Arg Val Thr Gly Leu Asp Phe Ile Pro Gly Leu His Pro
         35                  40                  45

Ile Leu Ser Leu Ser Lys Met Asp Gln Thr Leu Ala Val Tyr Gln Gln
     50                  55                  60

Ile Leu Thr Ser Leu Pro Ser Gln Asn Val Leu Gln Ile Ala His Asp
 65                  70                  75                  80

Leu Glu Asn Leu Arg Asp Leu Leu His Leu Leu Ala Phe Ser Lys Ser
                 85                  90                  95

Cys Ser Leu Pro Gln Thr Arg Gly Leu Gln Lys Pro Glu Ser Leu Asp
                100                 105                 110

Gly Val Leu Glu Ala Ser Leu Tyr Ser Thr Glu Val Val Ala Leu Ser
            115                 120                 125

Arg Leu Gln Gly Ser Leu Gln Asp Ile Leu Gln Gln Leu Asp Leu Ser
        130                 135                 140

Pro Glu Cys
145
```

METHODS FOR IMPROVING BRAIN FUNCTION USING LEPTIN OR ANALOGS THEREOF

BACKGROUND OF THE INVENTION (1) Field of the Invention

The present invention relates to a drug for improvement of brain function which includes leptin of the mammals as an effective component, and particularly to such a drug for improvement of brain function which is effective to prevent and treat dementia such as Alzheimer's disease and cerebral apoplexy, etc., and to cure sequelae of cerebral apoplexy.

(2) Prior Art

The advancing aging society is becoming serious as a social problem in recent years. With the advancement of the aging society, the number of patients of dementia such as Alzheimer's disease is showing a tendency to increase, and a development of a remedy for these dementia is in an urgent need. In the meantime, existence of leptin has been known from a long time ago. It has been made clear by various studies that leptin is found at an exceptionally high density only in fat tissue and that it acts to regulate food intake and to increase energy consumption, therefore, it is under development for use as an anti-obesity drug and antidiabetics.

SUMMARY OF THE INVENTION

The inventors of this invention have found, as a result of further earnest study, that leptin of mammals has an action to improve brain function which is effective to prevent and to treat dementia such as Alzheimer's disease and cerebral apoplexy, etc., and to cure sequelae of apoplexy, in addition to the known actions to regulate food intake and to increase energy consumption.

The drug for improvement of brain function of this invention contains leptin of the mammals as an effective component. The above-mentioned leptins of the mammals are highly preserved by 84% in mouse-human and by 96% in mouse-rat in the homology of amino-acid level, and are known to be the protein with high homology, and are recognized to show the same physiological actions even when administered to the different kinds of animals. Therefore, as the leptin of mammals of this invention, leptin of any kinds of mammals is applicable, in which the amino acid sequence of the leptin of the animals is substantially homologous with human leptin and the physiological action of the leptin is recognized to be the same with that of human leptin. For example, mouse leptin indicated by sequence ID number 2 or rat leptin indicated by sequence ID number 3 is also applicable as well as the human leptin indicated by sequence ID number 1.

The leptin of this invention includes analogue peptide of the above-mentioned leptin, as well as the polypeptide which exists in vivo as indicated by the above-mentioned sequence ID numbers from 1 to 3 known as mature leptin in vivo. In other words, the essence of this invention is that the leptin of the mammals being a product of obese gene has, for the first time, been found to be useful as a drug for improvement of brain function. Further, the analogue peptide of leptin, which is substantially homologous with mature leptin existing in vivo and shows physiological actions similar to the mature leptin in vivo, is also included in this invention.

The human leptin indicated by the above-mentioned sequence ID number 1 is expressed as precursor polypeptide consisting of 167 amino acid residue in a cell as a product of obese gene, after which signal peptide consisting of 21 amino acid residue of the amino terminus is cut off, and is secreted in vivo as mature protein consisting of 146 amino acid residue.

The above-mentioned analogue peptide of leptin means the polypeptide in which one or plural amino acid residue/residues is/are added to, is/are removed from, or is/are replaced with the above-mentioned mature leptin in vivo. To be more specific, leptins indicated by sequence ID numbers from 4 to 6 in which methionine is added to the amino terminus of the above-mentioned leptins is one example.

As the drug for improvement of brain function of this invention, the above-mentioned leptin of mammals may include the pharmaceutically acceptable salts thereof, for example, salts with alkaline metals such as sodium and potassium, salts with alkaline earth metals such as calcium and magnesium, salts with metals such as alminum and acid addition salts with hydrochloric acid, sulfuric acid, nitric acid, hydrobromic acid, thiocyanic acid, boric acid, formic acid, acetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid and the like. These salts can be produced from the above-mentioned free leptin, or can be transformed to each other by the methods known to public.

The drug for improvement of brain function of this invention may contain at least one of the above-mentioned leptin of mammals and the analogue peptide of the above-mentioned leptin of mammals. They can either be used independently or together. When the protein which is prepared from a different kind of mammals is applied for medical treatment of man, there are not a few cases in which it causes allograft rejection or shock symptoms on the basis of immunity defense systems, therefore human leptin, namely, human leptin and analogue peptide thereof are preferable, analogue peptide of human leptin is more preferable, and analogue peptide of human leptin indicated by the sequence ID number 4 is particularly preferable.

Processes for obtaining the leptin of this invention are, for example, a process by purification and isolation from living bodies or from cultured cells, a peptide synthesis process such as a solid-phase or a liquid-phase peptide synthesis process, and a production process by use of genetic recombination technology, etc. Since the leptin of this invention consists of many amino acid residues, the production process by use of genetic recombination technology is industrially preferable.

As expression systems (host-vector systems) for production of leptine and analogue peptide thereof by use of genetic recombination engineering, there are expression systems of bacteria, yeast, insect cell and mammal cell, for example. And it is possible to obtain analogue peptide of leptine indicated by the above-mentioned sequence ID numbers from 4 to 6 by use of genetic recombination engineering, namely for example, by ligating cDNA, coding the above-mentioned sequence ID numbers from 4 to 6, with an optional expression vector and then transfecting the vector to a proper host cell.

As to the above-mentioned cDNA which codes the leptin of this invention, human and murine leptin cDNA is mentioned in PCT Japanese publication No.9-506264, and rat cDNA is mentioned in the literature of Ogawa etc. [J. Clin. Invest., page 1647, volume 96 (year 1995] etc.

The process for genetic technological production of recombinant leptin by use of leptin gene is also described in detail in the above-mentioned publication and others. Leptin of this invention can be obtained by producing in accordance with these known processes, and some of the recombinant leptins are also available in market.

For example, it is possible to obtain human recombinant leptin indicated by sequence ID number 4, in which methionine being amino acid corresponding to initiation codon is connected to the amino terminal of polypeptide indicated by sequence ID number 1, by using cDNA, wherein the necessary initiation codon is connected to the head of the cDNA corresponding to the mature protein indicated by sequence ID number 1.

In order to ascertain whether the polypepide obtained from the above-mentioned process has the intended amino acid sequence or not, the already known processes are applied. For example, it is possible to identify the amino acid sequence of the obtained polypeptide chain by fragmentating the polypeptide chain obtained as mentioned above by using a reagent which has substrate specificity such as cyanide bromide or enzyme like trypsin, purifying by high performance liquid chromatography to isolate homogeneous peptide, and identifying amino acid sequence of these peptide fragments by automatic Edman method.

The drug for improvement of brain function of this invention is usually used by combining proper pharmaceutical carrier or diluent, and is formulated by the known process. On prescription, the drug for improvement of brain function of this invention may be used either solely or jointly, or in combination with the other drugs. As the drug for improvement of brain function of this invention is a peptide preparation, it is general to formulate as an injection. It could be prepared in a form of solution or suspension in aqueous or non-aqueous solvent such as distilled water for injection, physiological saline, Ringer solution, vegetable oil, synthetic fatty acid glyceride, higher fatty acid ester, or propylene glycol. Further, drug additives such as prevailing stabilizer, buffer, suspension agent, isotonic agent, pH modifier, preservatives may also be added. In addition to injection, sublingual tablet and nebulizer, which are absorbed through oral cavity mucus membrane and nose mucus membrane, are sometimes used for peptide drug, to which this invention can also be applied. Furthermore, it is possible to prepare the other forms of medicine, depending on diseases, which is the best for the treatment thereof like oral medicine by special preparation so that it is not decomposed even when administered orally. Advantages:

The drug for improvement of brain function of this invention has a superior effect on improvement of learning and memory, as evidenced by the tests described in detail hereinafter. The drug is active in a Passive Avoidance Learning Test. A therapeutic amount of the drug may be administered to a patient known to be in need of improvement of memory or treatment of memory deterioration. Further, the drug for improvement of brain function of this invention has high usefulness to cure diseases which cause deterioration of brain function like brain degeneration diseases such as Alzheimer's disease, senile dementia, Pick's disease, Huntington's chorea, Parkinson disease, parkinsonism dementia syndrome, progressive subcortical gliosis, progressive supranuclear palsy, thalamic degeneration syndrome, hereditary aphasia, myoclonus epilepsy; cerebrovascular disorders like celebral arteriosclerosis; cerebral infection diseases and cerebral inflammatory diseases like general paresis, various encephalitis gliomgs, Creutzfeldt-Jakob disease, subacute sclerosing panencephalitis, progressive mulifocal leukoence phalopathy, systemic lupus erythematosus; poisonous brain troubles like chronic alcoholism, carbon monoxide poisoning, heavy metal poisoning; ischemic brain diseases like head injury, epilepsy, brain tumor, intracranial hematoma, dialysis encephalopathy, brain infarction, and cerebral thrombosisa; and to improve various symptoms caused by these diseases like memory deterioration, aphasia, disturbance of consciousness, depression, apathy, delusion, and confusion.

BRIEF DESCRIPTION OF THE DRAWINGS

The drawings show embodiments of this invention in which.

DETAILED DESCRIPTION OF PREFERRED EMBODIMENTS

Following is detailed description about the results of the investigation on the effect of brain function improvement of the drug for improvement of brain function of this invention, in which normal rats (male, Wister strain, 150–200 g body weight) were used. Analogue peptide of leptin of mouse indicated by sequence ID number 5 (manufactured by Pepro Tech EC Ltd., and the tradename is Recombinant Murine Leptin) was used as a drug for improvement of brain function.

(1) Passive Avoidance Learning Test

Figure 1:
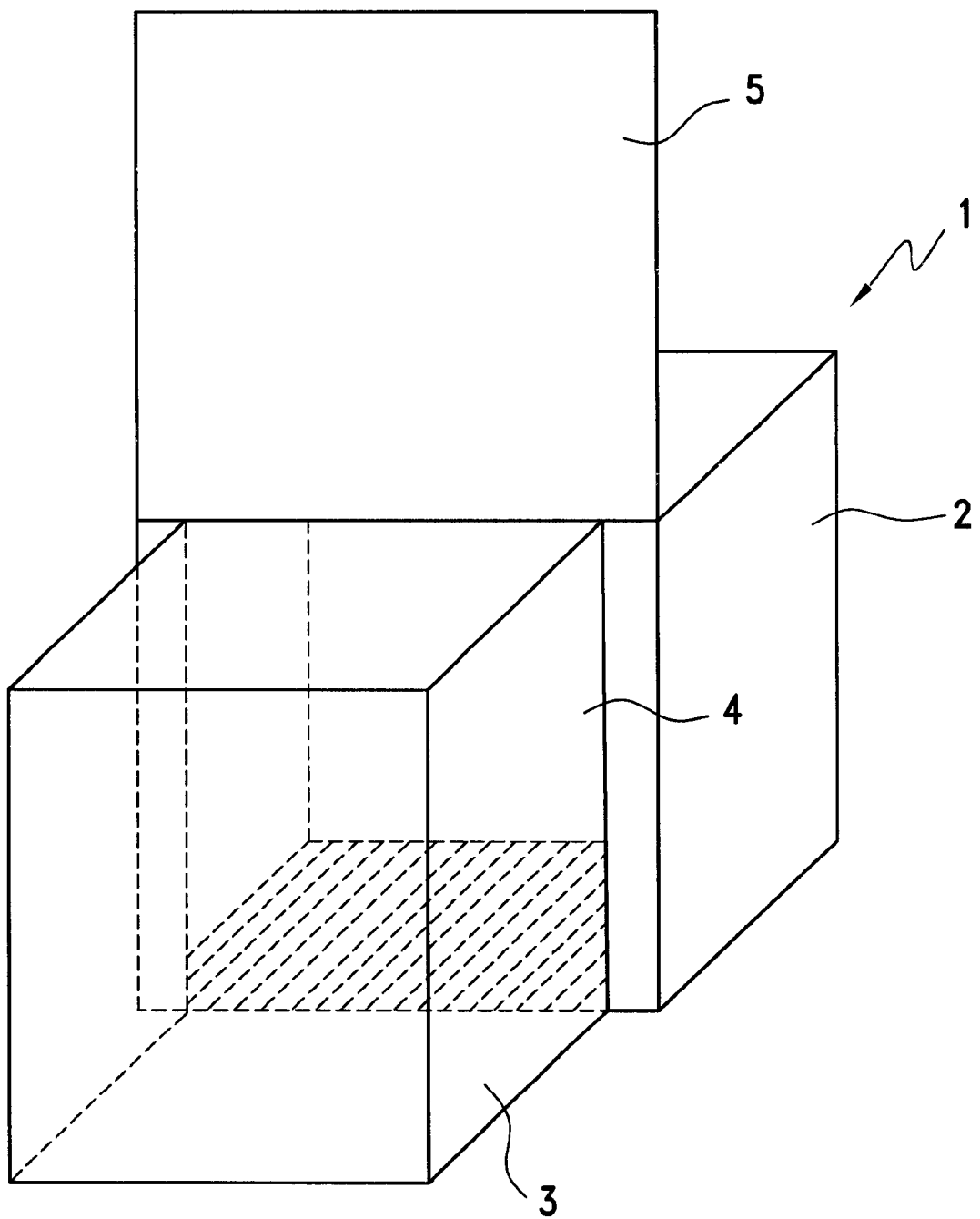
FIG. 1 is a perspective view of a testing device for a passive avoidance learning test.

A testing device 1 used in this test, as shown in FIG. 1, consists of a dark box 2 which is 30 cm long×30 cm wide×30 cm high, a light box 3 which is connected to the dark box 2 and is 24 cm long×24 cm wide×30 cm high, a through opening 4 at the connecting face between the dark box 2 and the light box 3, and a diaphragm 5 arranged at the through opening 4 which can freely close and open the through opening 4. On an inner surface of the light box 3, a lighting equipment of 10 luxes (not shown in the drawing) is equipped. In other words, the testing device 1 is so constructed that the light box 3 is always lighted up by the lighting equipment, and when the through opening 4 is closed with the diaphragm 5, light from the light box 3 is cut off and inside the dark box 2 becomes totally dark.

Using such a testing device, in a situation that the through opening 4 was closed by placing the diaphragm 5 between the light box 3 and the dark box 2, at first, a rat was left in the light box 3 which was lighted up with the lighting equipment of 10 luxes. After 30 seconds, the diaphragm 5 was removed to open the through opening 4 and to make the light box 3 and the dark box 2 through, and then took the time that the rat moved from the light box 3 into the dark box 2. After the rat entered into the dark box 2, the through opening 4 was closed with the diaphragm 5 and electroshock was given to the rat over 2 seconds by sending an electric current of 0.06–0.6 mA to the inner bottom surface of the dark box 2.

Figure 2:
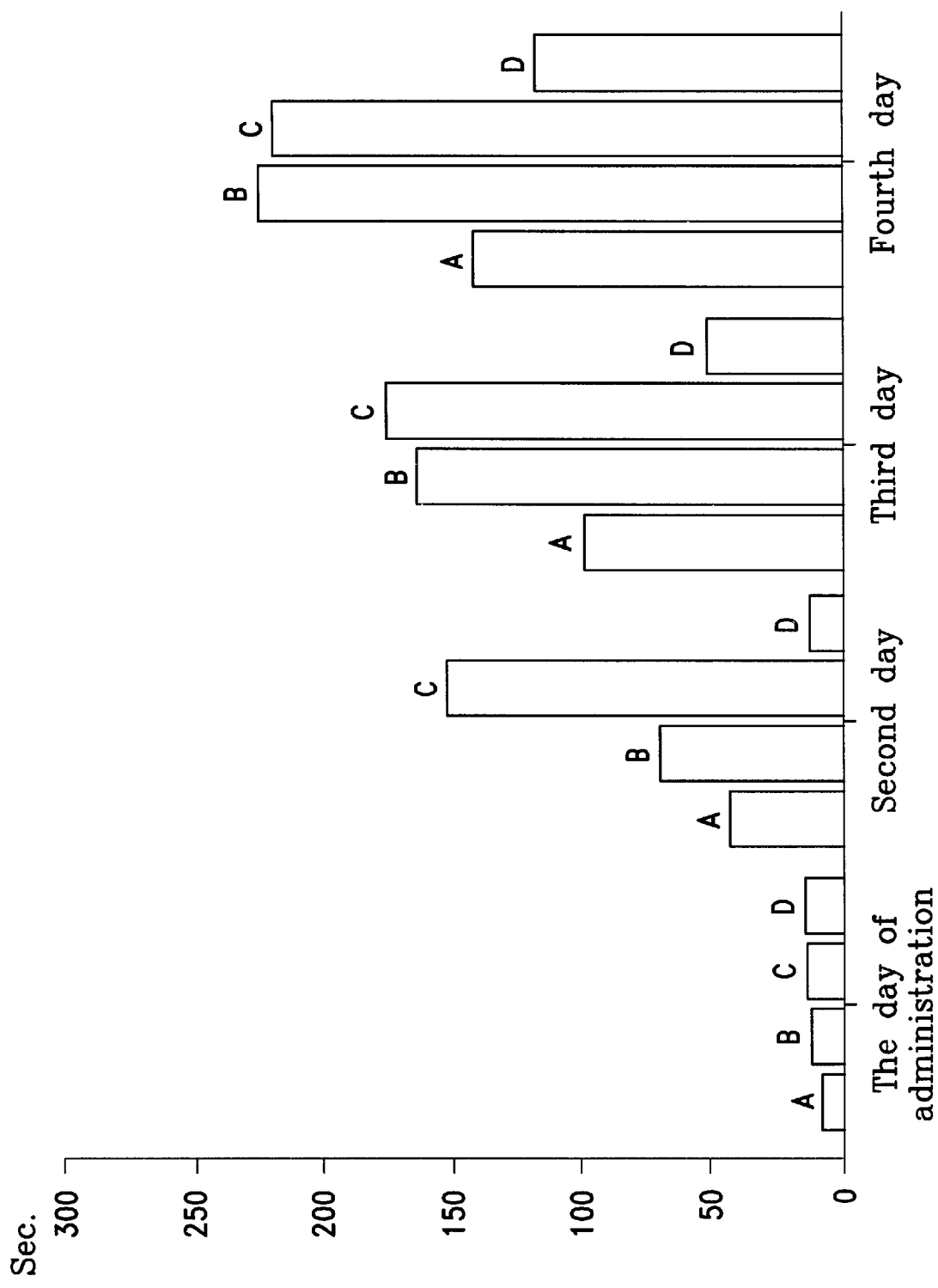
FIG. 2 is a graph showing a result of the measurement of the passive avoidance learning test.
Figure 3:
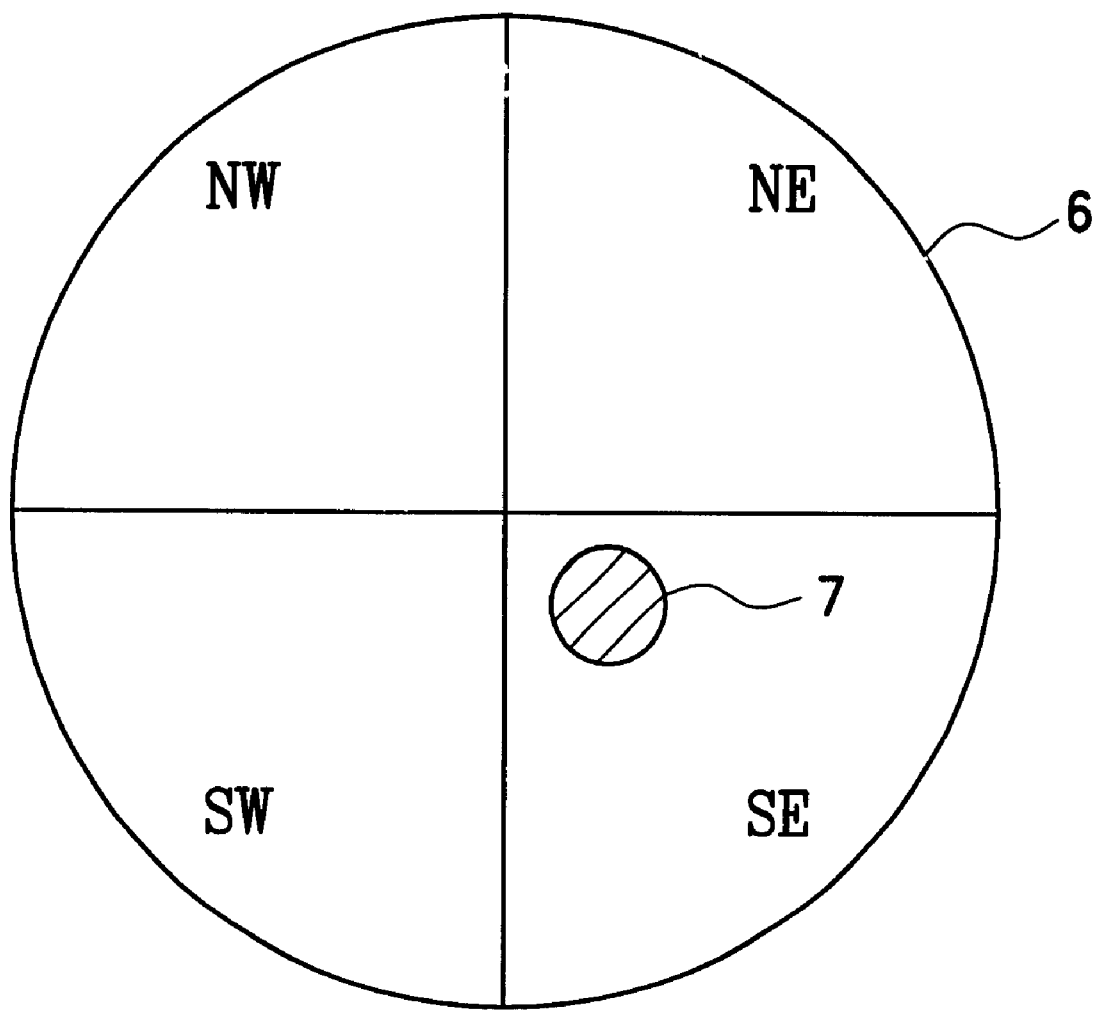
FIG. 3 is a plan view showing a circular testing pool which was used in the water maze learning test.

28 normal rats as mentioned above (male, Wister strain, 150–200 g body weight) were divided into four groups A, B, C, and D of 7 each. Then 0.5 μg/kg of analogue peptide of murine leptin indicated by sequence ID number 5 was administered intravenously to the each of the 7 rats in the group A every day, 5.0 μg/kg of analogue peptide of murine leptin indicated by sequence ID number 5 was administered to the each of the 7 rats in the group B every day, and 50 μg/kg of analogue peptide of murine leptin indicated by sequence ID number 5 was administered to the each of the 7 rats in the Group C every day. The above-mentioned test was conducted on each rat every day for 4 days. The above-mentioned test was conducted 30 minutes after analogue peptide of leptin indicated by sequence ID number 5 was administered to the rats. The above-mentioned test was conducted on the 7 rats in the group D without administration of analogue peptide of murine leptin indicated by sequence ID number 5 as a control group for comparison. The result of the above-mentioned test is shown by a graph in FIG. 2. (A vertical line in the graph shows a mean value of rats in a group.)

In the meantime, rats prefer the dark, however, in the above-mentioned test, as electroshock is given after entering into the dark box 2, the better memory a rat has, the longer the time for entering into the dark box 2 becomes, as the rat with better memory remembers the above-mentioned electroshock.

(2) Water Maze Learning Test (Morris Water Maze Learning Test)

In an SE section, which is mentioned later, of a plane circular testing pool 6 having a diameter of 150 cm and a depth of 40 cm, a plane circular platform 7 with a radius of 12 cm were placed 1 cm below the surface of water, and small beads of styrene foam were evenly spreaded over the water surface so that the platform 7 were not able to be seen by the rat. Spacial clues around the device (testers, tables, fluorescent lamps, testing devices, etc.) were always kept unchanged over the period of the test.

On the day of the test, the circular testing pool 6 was divided into 4 equal sections, being an NW section, an SW section, an SE section and an NE section. Then, a rat was made swim from starting points of the above-mentioned 4 sections (NW secition, SW section, SE section and NE section) of the circular testing pool 6, at 10 minutes' intervals, and then the time was measured for the rat to reach the platform 7, and total time of the 4 times of the test was calculated. At the same time, a distance of swimming until the rat reached the platform 7 was also measured.

Figure 4:
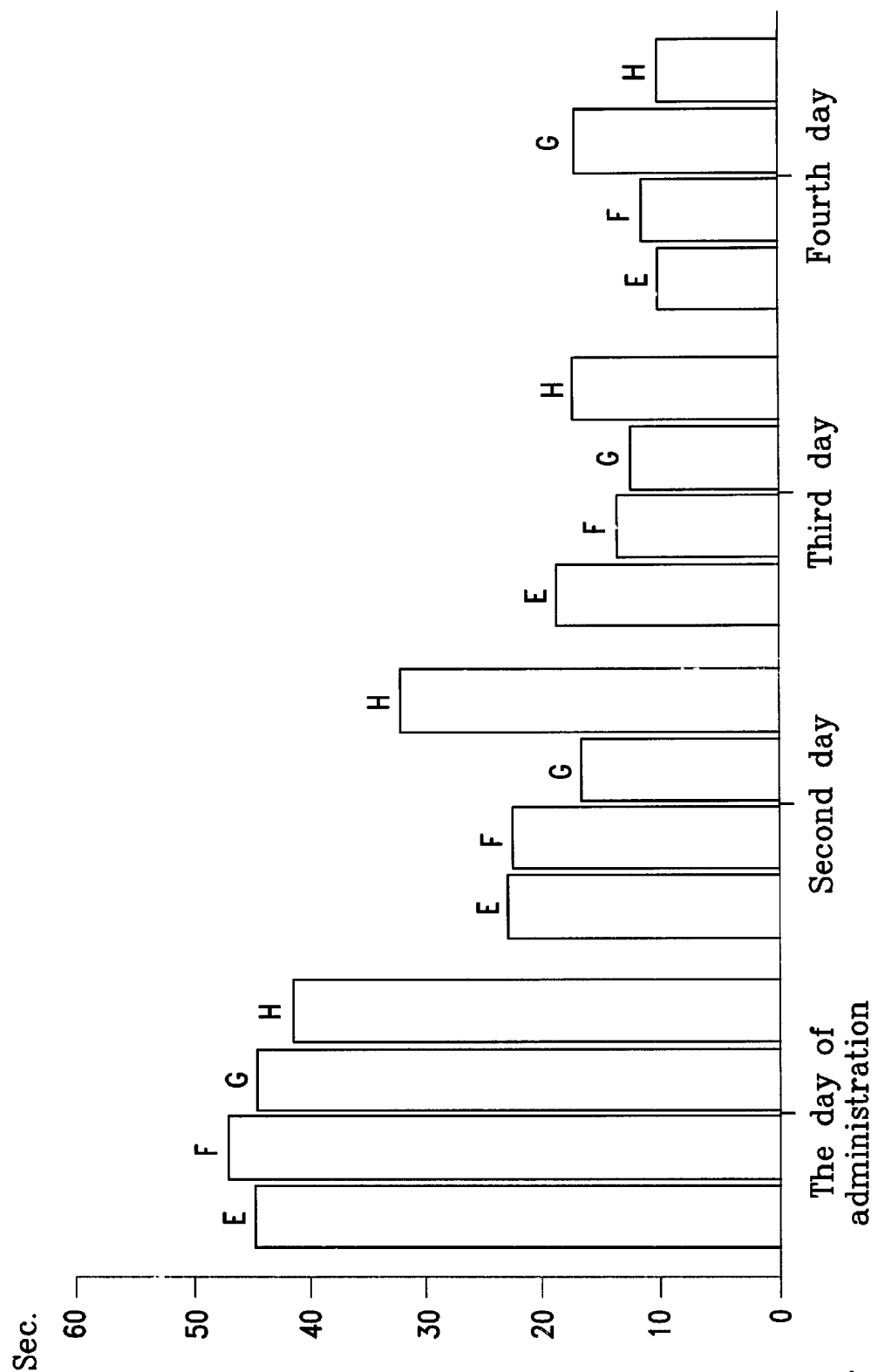
FIG. 4 is a graph showing the time to reach the platform in the water maze learning test.
Figure 5:
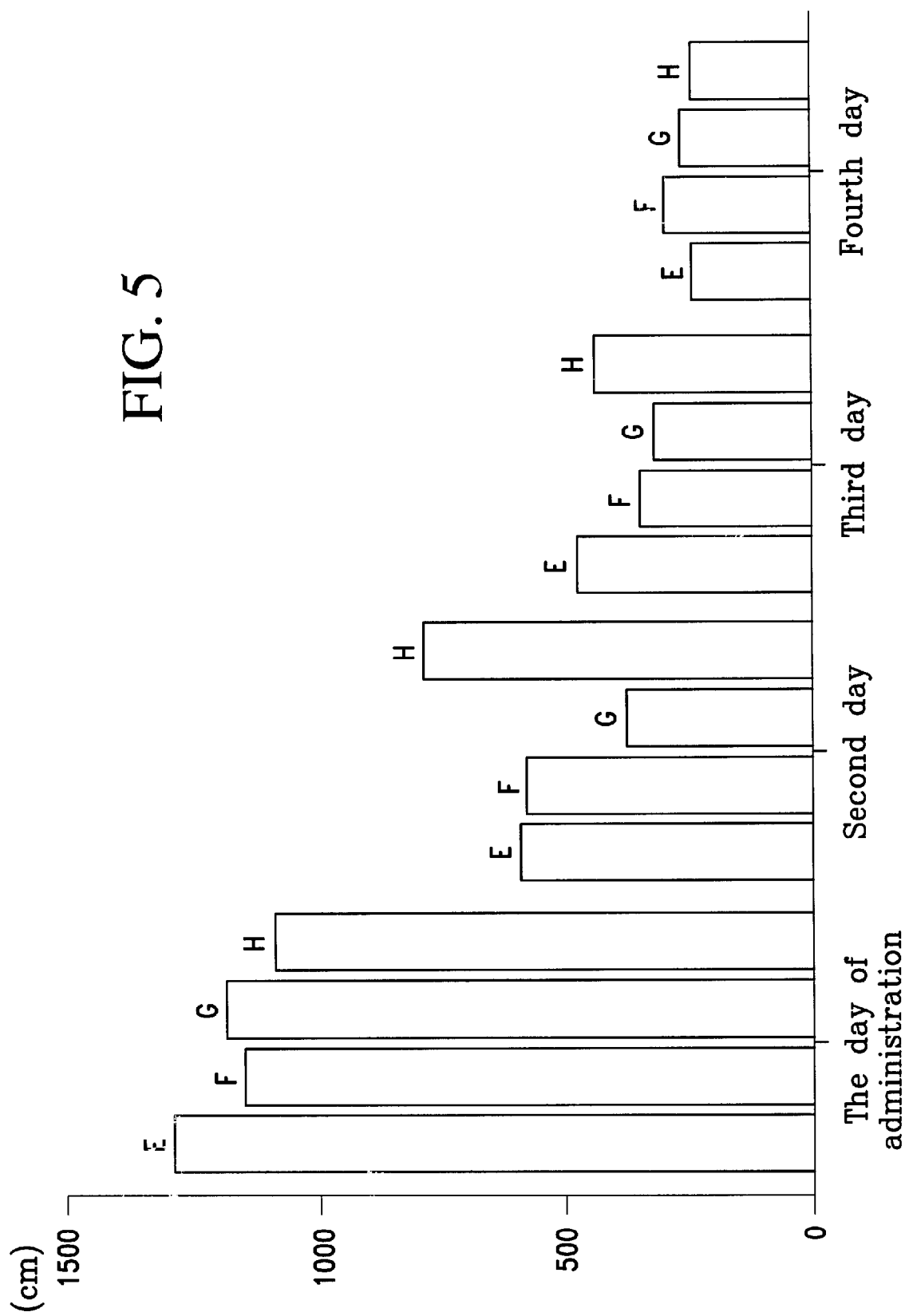
FIG. 5 is a graph showing the distance of swimming to reach the platform in the water maze learning test.

56 normal rats as mentioned above (male, Wister strain, 150–200 g body weight) were divided into groups E, F, G, and H. Then 0.5 μg/kg of analogue peptide of murine leptin indicated by sequence ID number 5 was administered intravenously to each of the 16 rats in the group E every day, 5.0 μg/kg of analogue peptide of murine leptin indicated by sequence ID number 5 was administered to each of the 20 rats in the group F every day, and 50 μg/kg of analogue peptide of murine leptin indicated by sequence ID number 5 was administered to each of the 20 rats in the Group G every day. And then the above-mentioned test was conducted on each rat every day for 4 days. The above-mentioned test was conducted 30 minutes after analogue peptide of leptin indicated by sequence ID number 5 was administered to the rats. The above-mentioned test was conducted on the 20 rats in the group H without administration of analogue peptide of murine leptin indicated by sequence ID number 5 as a control group for comparison. The result of the above-mentioned test is shown by the graphs of FIGS. 4 and 5. (The vertical lines in the graphs show mean values of rats in a group.)

The better memory a rat has, the shorter the distance and the time the rat swim before it reaches the platform 7, as the rat with better memory remembers the location of the platform 7 of the circular testing pool 6.

As indicated by the result shown in FIGS. 4 and 5, the time and the distance of swimming and floating of the groups E, F, and G, which were administered analogue peptide of murine leptin indicated by sequence ID number 5, are clearly shortened on the second day, compared to the control group H.

(3) Electro-physiologcal Test by Use of Hippocampus Slices

A brain of a rat was quickly taken out and a slice of hippocampus section with a thickness of 400 μm was prepared by a slice specimen preparation device. Under the atmosphere of 95 cubic volume $\%O_2$ and 5 cubic volume $\%CO_2$, the above-mentioned slice of hippocampus was fixed in a chamber in which Krebs Ringer solution of 34° C. was refluxed at 3 ml/min. Then analogue peptide of murine leptin indicated by sequence ID number 5 was added by $1/10^{12}$M to the slice of hippocampus. After 15 minutes, a stimulus electrode was placed at the Schaffer collateral pathway, and a recorder glass microelectrode with a diameter of about 5 μm at the tip was placed at the synapse of CA1.

Figure 6:
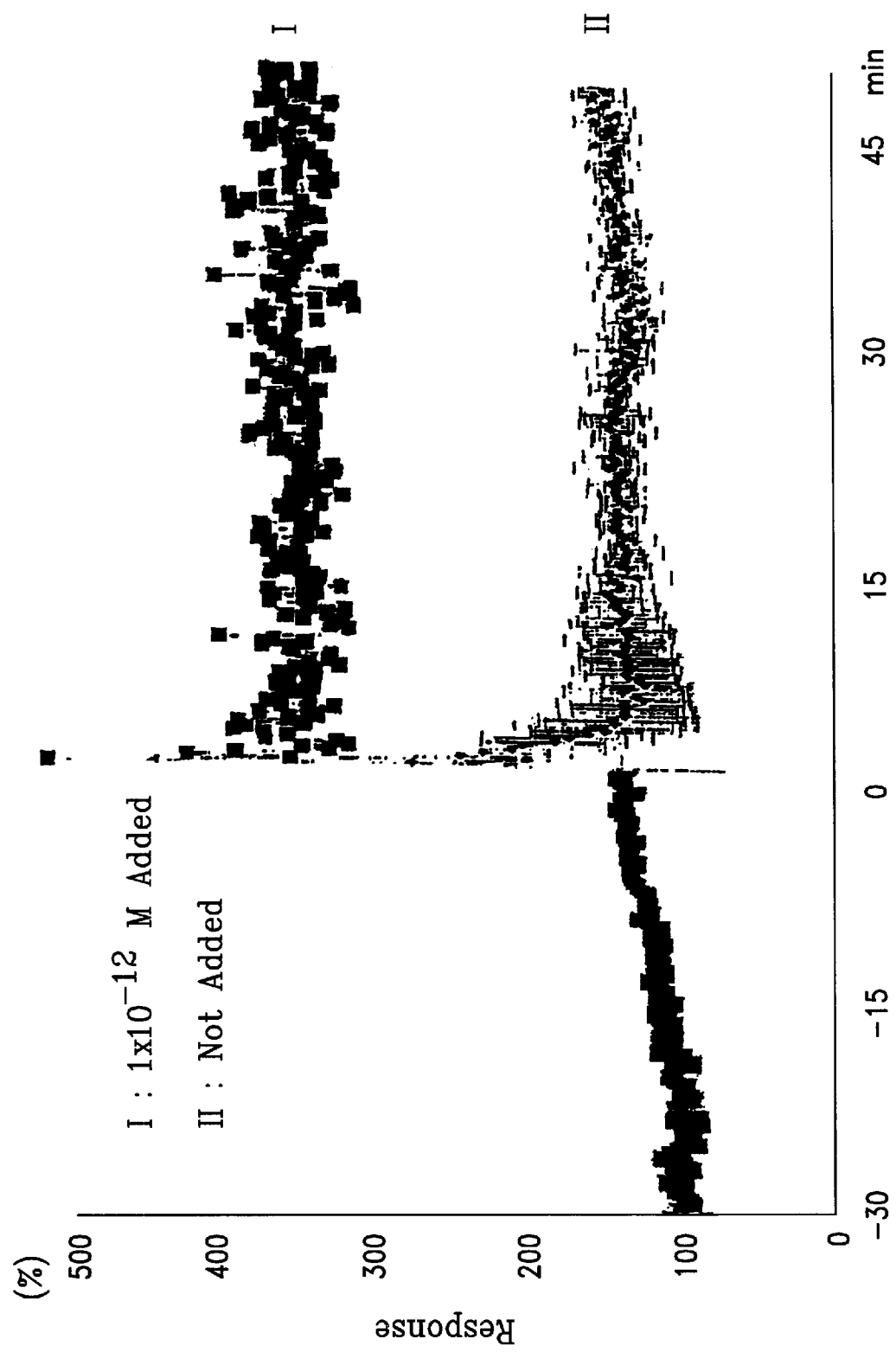
FIG. 6 is a graph showing the result of the electro-phisiological test by use of hippocampus slices.

And then, a square short impulse (sustaining period 50 μsec, intensity 10–15V) was given to the Schaffer collateral pathway by a stimulus electrode once every 15 seconds, and synaptic potential of CA1 neuron was measured by the above-mentioned recorder glass micro-electrode. After the amplitude of the synaptic potential became stable, tetanic stimulation (sustaining 1 second at 100 Hz) being 10 square short pulses were given, and synaptic potential was measured by the above-mentioned recorder glass microelectrode once every 15 seconds, and the result is shown in FIG. 6. Further, similar measurement of synaptic potential was conducted also in the case when analogue peptide of murine leptin indicated by sequence ID number 5 was not added to the slice of hippocampus and the result is shown in FIG. 6. In FIG. 6, the time when tetanic stimulation was given to the slice of hippocampus is set 0 second, before which is indicated by minus, and after which is indicated by plus. In the above-mentioned FIG. 6, in case the amplitude of the synaptic potential was increased by 110% by the tetanic stimulation for more than 30 minutes after the tetanic stimulation, it can be concluded that long term potentiation of synaptic potential is facilitated.

(4) Long Term Depression Test

Figure 7:
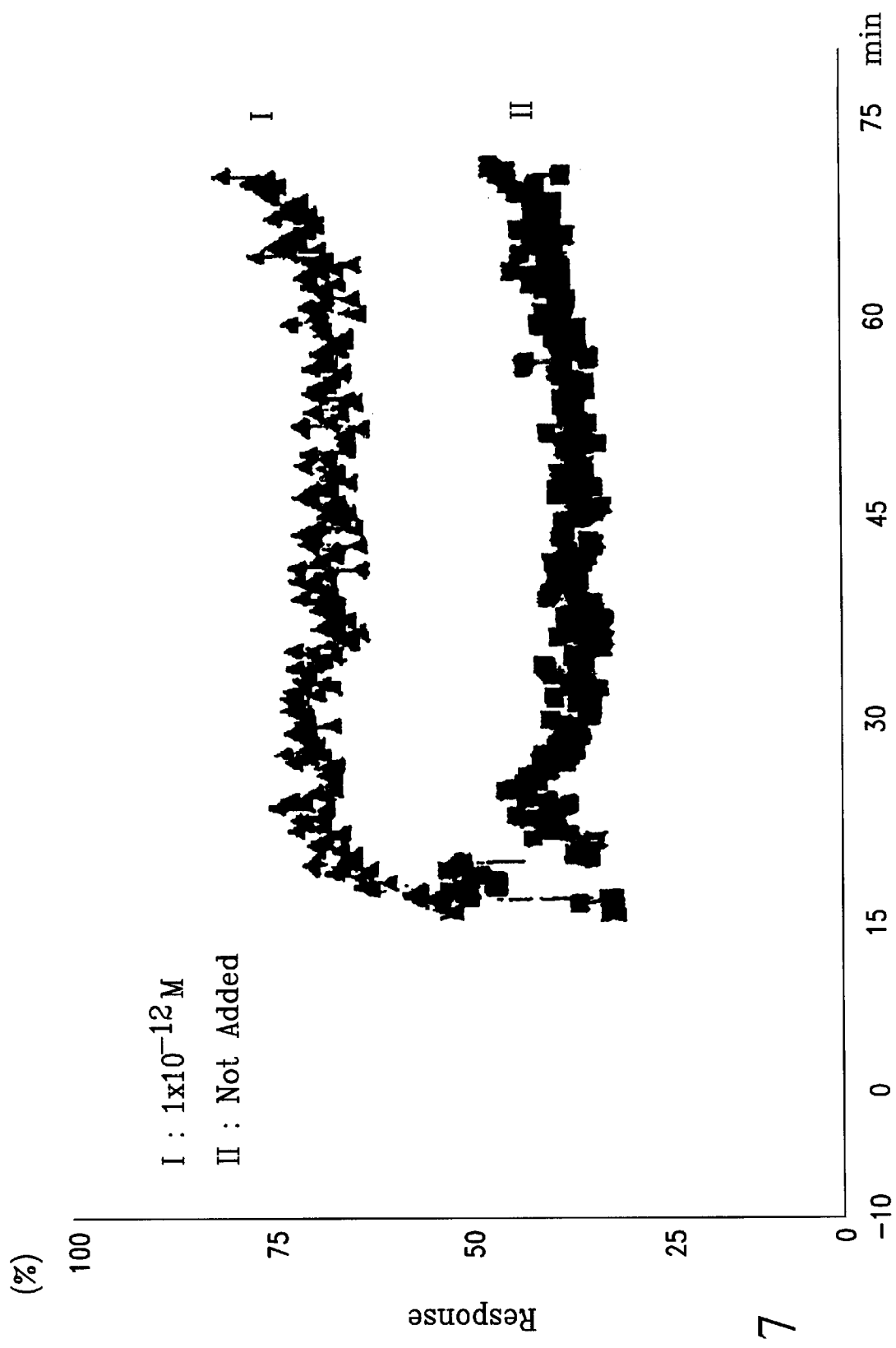
FIG. 7 is a graph showing the result of the long-term depression test.

A brain of a rat was quickly taken out and a slice of hippocampus section with a thickness of 400 μm was prepared by a slice specimen preparation device. Under the atmosphere of 95 cubic volume $\%O_2$ and 5 cubic volume $\%CO_2$, the above-mentioned slice of hippocampus was fixed in a chamber in which Krebs Ringer solution of 34° C. was refluxed at 3 ml/min. Then analogue peptide of murine leptin indicated by sequence ID number 5 was added by $1/10^{12}$M to the slice of hippocampus. After 15 minutes, a stimulus electrode was placed at the Schaffer collateral pathway, and a recorder glass microelectrode with a diameter of about 5 μm at the tip was placed at the synapse of CA1. And then, a square short impulse (sustaining period 50 μsec, intensity 10–15V) was given to the Schaffer collateral pathway by a stimulus electrode once every 15 seconds, and synaptic potential of CA1 neuron was measured by the above-mentioned recorder glass microelectrode. After the amplitude of the synaptic potential became stable, tetanic stimulation was given once every second over 15 minutes, and synaptic potential was measured by the above-mentioned recorder glass microelectrode once every 15 seconds. The result is shown in FIG. 7. Further, similar measurement of synaptic potential was conducted also in the case when analogue peptide of murine leptin indicated by sequence ID number 5 was not added to the slice of hippocampus and the result is shown in FIG. 7.

What is claimed is:

1. A method for improving memory or treating memory deterioration comprising administering to a patient known to be in need of such improvement or treatment a therapeutic amount of:

at least one leptin selected from the group consisting of any one of SEQ. ID. No. 1, SEQ. ID No. 2, SEQ. ID. No. 3, SEQ. ID. No. 4, SEQ. ID. No. 5, and SEQ. ID. No. 6, an analogue which differs by a single conservative amino acid substitution from any one of SEQ. ID. No. 1, SEQ. ID No. 2, SEQ. ID. No. 3, SEQ. ID. No. 4, SEQ. ID. No. 5, and SEQ. ID. No. 6, wherein said analogue is active in a Passive Avoidance Learning Test, at least one leptin that is active in a Passive Avoidance Learning Test and is selected from the group consisting of a leptin having an amino acid homology of at least 99% with any one of SEQ. ID. No. 1, SEQ. ID. No. 2, SEQ. ID. No. 3, SEQ. ID. No. 4, SEQ. ID. No. 5 and SEQ. ID. No. 6, or pharmaceutically acceptable salts thereof.

2. A method as claimed in claim 1 wherein said at least one leptin is selected from the group consisting of SEQ. ID. No. 1, SEQ. ID No. 2 and SEQ. ID. No. 3.

3. A method as claimed in claim 1, wherein said at least one leptin is an analogue which differs by a single conservative amino acid substitution from any one of SEQ. ID. No.1, SEQ. ID No. 2, SEQ. ID. No. 3, SEQ. ID. No. 4, SEQ. ID. No. 5, and SEQ. ID. No. 6, wherein said analogue is active in a Passive Avoidance Learning Test.

4. A method as claimed in claim 3 wherein said analogue differing conservatively differs from any one of SEQ. ID. Nos. 1, 2 and 3 by the addition of a single amino acid residue.

5. A method as claimed in claim 4 wherein said analogue differs from any one of SEQ. ID. No. 1, SEQ. ID. No. 2 and SEQ. ID. No. 3 by the addition of methionine to the amino terminus thereof.

6. A method for improving memory or treating memory deterioration comprising administering to a patient known to be in need of such improvement or treatment a therapeutic amount of at least one leptin selected from the group consisting of a leptin having an amino acid homology of at least 99% with any one of SEQ. ID. No. 1, SEQ. ID No. 2, SEQ. ID. No. 3, SEQ. ID. No. 4, SEQ. ID. No. 5, and SEQ. ID. No. 6 and pharmaceutically acceptable salts thereof, wherein said at least one leptin is active in a Passive Avoidance Learning Test.

7. A method as claimed in claim 1 wherein said at least one leptin is selected from the group consisting of any one of SEQ. ID. Nos. 1 and 4 and pharmaceutically acceptable salts thereof.

8. A method as claimed in claim 1 wherein said at least one leptin is selected from the group consisting of SEQ. ID. No. 1 and pharmaceutically acceptable salts thereof.

9. A method as claimed in claim 1 wherein said patient is administered a leptin that is SEQ. ID. No. 4 or a pharmaceutically acceptable salt thereof.

10. A method as claimed in claim 1 wherein said at least one leptin comprises at least one member selected from the group consisting of SEQ. ID. No. 1, SEQ. ID. No. 2, SEQ. ID. No. 3, SEQ. ID. No. 4, SEQ. ID. No. 5, SEQ. ID. No. 6, and pharmaceutically acceptable salts thereof.

11. A method as claimed in claim 6 wherein said at least one leptin is selected from the group consisting of a leptin having an amino acid homology of at least 99% with any one of SEQ. ID. No. 1 and pharmaceutically acceptable salts thereof.

12. A method for improving memory, comprising:

identifying a patient in need of memory improvement; and administering to the patient a memory-improving amount of at least one leptin selected from the group consisting of SEQ. ID. No. 1, SEQ. ID No. 2, SEQ. ID. No. 3, SEQ. ID. No. 4, SEQ. ID. No. 5, SEQ. ID. No. 6, an analogue which differs by a single conservative amino acid substitution from any one of SEQ. ID. No. 1, SEQ. ID No. 2, SEQ. ID. No. 3, SEQ. ID. No. 4, SEQ. ID. No. 5, and SEQ. ID. No. 6, wherein said analogue is active in a Passive Avoidance Learning Test, at least one leptin that is active in a Passive Avoidance Learning Test and is selected from the group consisting of a leptin having an amino acid homology of at least 99% with any one of SEQ. ID. No. 1, SEQ. ID. No. 2, SEQ. ID. No. 3, SEQ. ID. No. 4, SEQ. ID. No. 5 and SEQ. ID. No. 6, and pharmaceutically acceptable salts thereof.

* * * * *